(12) United States Patent
Maienfisch et al.

(10) Patent No.: US 6,518,433 B1
(45) Date of Patent: Feb. 11, 2003

(54) PROCESS FOR THE PREPARATION OF NITROGUANIDINE DERIVATIVES

(75) Inventors: Peter Maienfisch, Rodersdorf (CH); Thomas Rapold, Wallbach (CH); Henry Szczepanski, Wallbach (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/646,441

(22) PCT Filed: Mar. 17, 1999

(86) PCT No.: PCT/EP99/01781
§ 371 (c)(1),
(2), (4) Date: Nov. 2, 2000

(87) PCT Pub. No.: WO99/47520
PCT Pub. Date: Sep. 23, 1999

(30) Foreign Application Priority Data

Mar. 19, 1998 (CH) .................................... 649/98

(51) Int. Cl.⁷ .................... C07D 401/12; C07D 405/12; C07D 417/12
(52) U.S. Cl. ................ 546/332; 549/491; 548/205; 546/264; 546/280; 546/283
(58) Field of Search ............... 544/8, 67; 546/306, 546/332, 264, 280, 283; 548/202, 205; 549/492, 491

(56) References Cited

U.S. PATENT DOCUMENTS

| | | | |
|---|---|---|---|
| 5,034,404 A | 7/1991 | Uneme et al. | 514/365 |
| 5,245,040 A | 9/1993 | Maienfisch et al. | 546/332 |
| 5,489,603 A | 2/1996 | Uneme et al. | 514/365 |
| 5,633,375 A | 5/1997 | Uneme et al. | 544/336 |
| 6,194,575 B1 | 2/2001 | Wollweber et al. | 544/180 |
| 6,252,072 B1 | 6/2001 | Maienfisch et al. | 544/180 |

FOREIGN PATENT DOCUMENTS

| | | |
|---|---|---|
| EP | 0 483 062 | 4/1992 |
| EP | 0 869 120 | 10/1998 |
| JP | 07224062 | * 8/1995 |
| WO | WO-97/40691 | * 11/1997 |
| WO | WO-99/09009 | * 2/1999 |

OTHER PUBLICATIONS

Moriie et al Chemical Abstract accession No. 1995:967179 for JP 07224062, 1995.*

* cited by examiner

Primary Examiner—John M. Ford
(74) Attorney, Agent, or Firm—William A. Teoli, Jr.; Rose M. Allen

(57) ABSTRACT

A process for the production of a compound of formula (I)

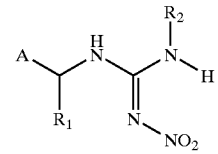

wherein
R₁ is hydrogen or C₁–C₄-alkyl;
R₂ is hydrogen, C₁–C₆-alkyl, C₂–C₆-alkenyl, C₂–C₆-alkinyl, C₃–C₆-cycloalkyl or a radical —CH₂B;
A is selected from the group consisting of 2-chloropyrid-5-yl, tetrahydrofuran-3-yl, 5-methyl-tetrahydrofuran-3-yl or 2-chlorothiazol-5-yl; and
B is phenyl, 3-pyridyl or thiazolyl, which are optionally substituted by one to three substituents selected from the group consisting of C₁–C₃-alkyl, C₁–C₃-halogenalkyl, cyclopropyl, halogencyclopropyl, C₂–C₃-alkenyl, C₂–C₃-alkinyl, C₁–C₃-alkoxy, C₂–C₃-halogenalkenyl, C₂–C₃-halogenalkinyl, C₁–C₃-halogenalkoxy, C₁–C₃-alkylthio, C₁–C₃-halogenalkylthio, allyloxy, propargyloxy, allylthio, propargylthio, halogenallyloxy, halogenallylthio, halogen, cyano or nitro;
and optionally the possible E/Z isomers, E/Z isomeric mixtures and/or tautomers thereof, respectively in free form or in salt form;
characterised in that a compound of formula (II)

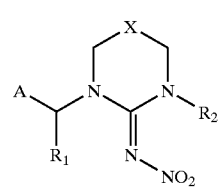

wherein
R¹, R₂ and A have the same significances as in formula (I), and
X is O or S;
is hydrolysed with a strong acid at a pH below 2; at a temperature between 50 and 100° C; and in a solvent selected from the group consisting of water, alcohols, ethers or mixtures thereof. The compounds of formula (I) are suitable for the preparation of pesticides.

7 Claims, No Drawings

PROCESS FOR THE PREPARATION OF NITROGUANIDINE DERIVATIVES

This application claims priority to PCT/EP99/01781, filed Mar. 17, 1999.

The invention relates to a process for the production of a compound of formula

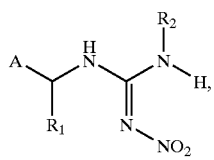

(I)

wherein $R_1$ is hydrogen or $C_1$–$C_4$-alkyl;

$R_2$ is hydrogen, $C_1$–$C_6$-alkyl, $C_2$–$C_6$-alkenyl, $C_2$–$C_6$-alkinyl, $C_3$–$C_6$cycloalkyl or a radical —$CH_2B$;

A is an unsubstituted aromatic or non-aromatic, monocyclic or bicyclic heterocyclic radical, or—depending on the substitution possibilities of the ring system—one which is mono- to penta-substituted by substituents selected from the group comprising halogen, $C_1$–$C_3$-alkyl, $C_1$–$C_3$-alkoxy, halogen-$C_1$–$C_3$-alkyl, $C_1$–$C_3$-halogenalkoxy, cyclopropyl, halogencyclopropyl, $C_2$–$C_3$-alkenyl, $C_2$–$C_3$-alkinyl, $C_2$–$C_3$-halogenalkenyl and $C_2$–$C_3$-halogenalkinyl, $C_1$–$C_3$alkylthio, $C_1$–$C_3$-halogenalkylthio, allyloxy, propargyloxy, allylthio, propargylthio, halogenallyloxy, halogenallylthio, cyano and nitro; and B is phenyl, 3-pyridyl or thiazolyl, which are optionally substituted by one to three substituents from the group comprising $C_1$–$C_3$-alkyl, $C_1$–$C_3$-halogenalkyl, cyclopropyl, halogencyclopropyl, $C_2$–$C_3$-alkenyl, $C_2$–$C_3$-alkinyl, $C_1$–$C_3$-alkoxy, $C_2$–$C_3$-halogenalkenyl, $C_2$–$C_3$-halogenalkinyl, $C_1$–$C_3$-halogenalkoxy, $C_1$–$C_3$-alkylthio, $C_1$–$C_3$-halogenalkylthio, allyloxy, propargyloxy, allylthio, propargylthio, halogenallyloxy, halogenallylthio, halogen, cyano and nitro;

and optionally the possible E/Z isomers, E/Z isomeric mixtures and/or tautomers thereof, respectively in free form or in salt form;

characterised in that a compound of formula

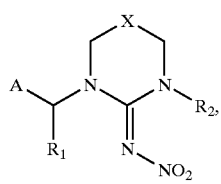

(II)

wherein $R_1$, $R_2$ and A have the same significances as in formula (I), and

X is O or S;

is hydrolysed with a strong acid.

The compounds of formula (I) may exist as E/Z isomers, e.g. in the two following isomeric forms

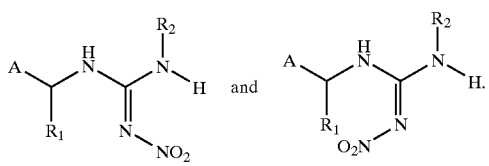

Accordingly, where reference is made hereinafter to the compounds of formula (I), this is understood to apply also to the corresponding E/Z isomers, even if the latter are not mentioned specifically in each case.

The compounds of formula (I) may also exist in part as tautomers, for example in the forms

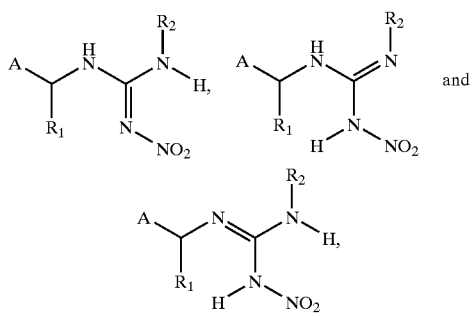

Accordingly, where reference is made hereinbefore and hereinafter to the compounds of formula (I), this is understood to apply also to the corresponding tautomers, even if the latter are not mentioned specifically in each case.

The compounds of formula (1), and optionally their E/Z isomers and tautomers, may exist as salts. Compounds of formula (I) which have at least one basic centre may form e.g. acid addition salts. These are formed for example with strong inorganic acids, such as mineral acids. e.g. sulphuric acid, a phosphoric acid or hydrohalic acid, with strong organic carboxylic acids, such as $C_1$–$C_4$-alkanecarboxylic acids that are optionally substituted, e.g. by halogen, for example acetic acid, such as optionally unsaturated dicarboxylic acids, e.g. oxalic acid, malonic acid, maleic acid, fumaric acid or phthalic acid, such as hydroxy-carboxylic acids, e.g. ascorbic acid, lactic acid, malic acid, tartaric acid or citric acid, or such as benzoic acid, or with organic sulphonic acids, such as $C_1$–$C_4$-alkane- or aryl-sulphonic acids that are optionally substituted, e.g. by halogen, for example methane- or p-to-luenesulphonic acid. Salts of compounds of formula (I) with acids of the types mentioned are preferably obtained during working up of the reaction mixtures.

In addition, compounds of formula (I) with at least one acidic group can form salts with bases. Suitable salts with bases are for example metal salts, such as alkali metal salts or alkaline earth metal salts, e.g. sodium, potassium or magnesium salts, or salts with ammonia or an organic amine, such as morpholine, piperidine, pyrrolidine, a mono-, di- or tri- lower alkyl amine, e.g. ethyl, diethyl, triethyl or dimethyl propyl amine, or with a mono-, di- or trihydroxy lower alkyl amine, e.g. mono-, di- or triethanol amine. Furthermore, if required, corresponding internal salts may be formed. Agrochemically advantageous salts are preferred within the scope of the invention. Where reference is made hereinbefore and hereinafter to the free compounds of formula (I) or their salts, this is understood to apply also to the corresponding salts or the free compounds of formula (I). The same applies to the E/Z isomerc and tautomers of compounds of formula (I) and their salts. The free form is preferred.

In the definition of the present formulae (I) and (II), the individual generic terms are to be understood as follows:

The halogen atoms considered as substituents are fluorine and chlorine and also bro-mine and iodine, whereby fluorine, chlorine and bromine are preferred, especially chlorine. Here, halogen is understood to be an independent substituent or part of a substituent as in halogenalkyl, halogenalkylthio, halogenalkoxy, halogencycloalkyl, halogenalkenyl, halogenalkinyl, halogenallyloxy or halogenallylthio. The alkyl, alkylthio, alkenyl, alkinyl and alkoxy radicals considered as substituents may be straight-chained or branched. Examples of such alkyls are methyl, ethyl, propyl, isopropyl, butyl, i-butyl, sec.-butyl or tert.-butyl. Suitable alkoxy radicals that may be mentioned are inter alia: methoxy, ethoxy, propoxy, iso-propoxy or butoxy and their isomers. Alkylthio is for example methylthio, ethylthio, isopropylthio, propylthio or the isomeric butylthio. If the alkyl, alkoxy, alkenyl, alkinyl or cycloalkyl groups considered as substituents are substituted by halogen, they can be only partly or even perhalogenated. The above-mentioned definitions apply to halogen, alkyl and alkoxy. Examples of the alkyl elements of these groups are methyl which is mono- to tri-substituted by fluorine, chlorine and/or bromine, for example $CHF_2$ or $CF_3$; ethyl which is mono- to penta-substituted by fluorine, chlorine and/or bromine, for example $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CGBrF$ or $CClFCHClF$; propyl or isopropyl which is mono- to hepta-substituted by fluorine, chlorine and/or bromine, for example $CH_2CHBrCH_2Br$, $CF_2CHFCF_3$, $CH_2CF_2CF_3$ or $CH(CF_3)_2$; butyl which is mono- to nona-substituted by fluorine, chlorine and/or bromine, or one of its isomers, for example $CF(CF_3)CHFCF_3$ or $CH_2(CF_2)_2CF_3$; 2-chlorocyclopropyl or 2,2-difluoro-cyclopropyl; 2,2-difluorovinyl, 2,2-dichlorovinyl, 2-chloroalkyl, 2,3-dichlorovinyl or 2,3-dibromovinyl.

If the defined alkyl, alkoxy or cycloalkyl groups are substituted by other substituents, they may be substituted once or more by the same or different substituents from those listed. There are preferably one or two further substituents present in the substituted groups. The cycloalkyl radicals considered as substituents are for example cyclopropyl, cyclobutyl, cyclopentyl or cyclohexyl. Alkenyl and alkinyl groups contain an unsaturated carbon-carbon bond. Typical representatives are allyl, methallyl or propargyl, but also vinyl and ethinyl. The double or triple bonds in allyloxy, propargyloxy, alkylthio or propargylthio are separated from the binding site to the hetero atom (O or S) preferably by a saturated carbon atom.

It is already known that, to produce 1,3-disubstituted 2-nitroguanidines, a further substituent may be introduced (e.g. by alkylation) into monosubstituted 2-nitroguanidines (see for example EP patent applications 0.375.907, 0.376.279 and 0.383.091). Owing to the presence of three reactive hydrogen atoms in the monosubstituted 2-nitroguanidines used as starting material in these reactions, the previously proposed substitution reactions of this kind are often non-selective and lead to undesired substitution products. The EP patent applications mentioned describe the preparation of 1,3-disubstituted 2-nitroguanidines by reacting monosubstituted nitroisothioureas with primary amines whilst cleaving mercaptan. However, these nitroisothiourea compounds which contain alkylthio leaving groups and are proposed as starting compounds in the known processes can only be obtained with difficulty.

In addition, in EP-A-0.483.062, a process for the preparation of the compounds of formula (I) is described, in which a triaza compound is hydrolysed. This process cannot be fully satisfactory in particular for ecological reasons.

It is now shown that the above-described processes for the preparation of compounds of formula (I) do not comply with the requirements regarding purity and yield, for which reason there is a need to provide an improved process for the preparation of these compounds from readily obtainable starting compounds.

It has now surprisingly been found that the process according to the invention is able to satisfy these requirements.

The hydrolysis process according to the invention is preferably carried out at a pH value of 2 or lower, under normal pressure and at a temperature of 0 to 120° C., preferably 50 to 100° C. It is preferable to operate in a mineral acid, especially hydrochloric acid, hydrobromic acid, sulphuric acid or phosphoric acid, or in aqueous solutions of alkylcarboxylic acids, halogenated alkylcarboxylic acids and sulphonic acids, especially in concentrated hydrochloric acid.

The reaction is carried out in a solvent or diluent which is inert towards the reaction components. Suitable solvents are, in particular, alcohols such as methanol, ethanol, propanol and iso-propanol, and especially water. Further appropriate solvents are e.g. ethers, such as tetrahydrofuran and dioxane, as well as other solvents which do not adversely affect the reaction. The solvents may also be used as mixtures. Preferably, a compound of formula (II) is hydrolysed in an aqueous medium or in a mixture of water with an alcohol.

The process according to the invention preferably serves to produce compounds of formula (I) in which the heterocyclic radical A is unsaturated and is bound by a carbon atom as a ring member to the basic substance. Preferred radicals A are pyridyl, thiazolyl, tetrahydrofuranyl, dihydrofuranyl, furanyl, n-oxido-pyridinio, oxazolyl, isoxazolyl, thienyl, morpholinyl, piperidinyl, pyridinyl and pyrazinyl; most preferably pyridyl, thiazolyl, tetrahydrofuranyl and n-oxido-pyridinio, especially 3-pyridyl, 2-halogenpyrid-5-yl, 2,3-dihalogenpyrid-5-yl, 2-halogenthiazol-5-yl, tetrahydrofuran-3-yl, 5-methyl-tetrahydrofuran-3-yl, 1-oxopyrid-3-yl, 1-oxo-2-halogen-pyrid-5-yl and 1-oxo-2,3-dihalogenpyrid-5-yl.

It is likewise preferable for the heterocycles A to bear one to three substituents which are selected from the group comprising halogen, $C_1$–$C_3$-alkyl, $C_1$–$C_3$-halogenalkyl, $C_1$–$C_3$-halo-genalkoxy and $C_1$–$C_3$-alkoxy.

In addition, compounds of formula (I) according to the invention are preferably produced, in which the radical B is a phenyl, pyridyl or thiazolyl radical which is unsubstituted or may be substituted by one to two radicals selected from the group comprising halogen, $C_1$–$C_3$-alkyl, $C_1$–$C_3$-halogenalkyl, $C_1$–$C_3$-halogenalkoxy and $C_1$–$C_3$-alkoxy.

Of the compounds of formula (I) to be produced according to the invention, those are notable wherein $R_1$ is hydrogen, $R_2$ is methyl, ethyl, n-propyl, n-butyl, allyl, propargyl or cyclopropyl and A is pyridyl, 1-oxopyridyl, tetrahydrofuranyl, thiazolyl or is pyridyl, 1-oxidopyridinio, tetrahydrofuranyl or thiazolyl which is substituted by one to three substituents selected from the group comprising halogen, $C_1$–$C_3$-alkyl, $C_1$–$C_3$-halogenalkyl, $C_1$–$C_3$-halogenalkoxy and $C_1$–$C_3$-alkoxy. In this sense, the production of those compounds of formula (I) in which a) $R_1$ is hydrogen;
b) $R_2$ is methyl;
c) A is 2-chloropyrid-5-yl, tetrahydrofuran-3-yl, 2-methyltetrahydrofuran-4-yl or 2-chlorothiazol-5-yl; and
d) X is O is also of interest.

The compounds of formula (I) produced according to the invention are valuable active ingredients in pest control, whilst being tolerated by mammals, fish and plants. The compounds of formula (I) are especially suitable for the control of insects and arachnids as are present on crop plants and ornamental in agriculture, especially in cotton, vegetable and fruit plantations, in woodland, in stock and material protection, as well as in the hygiene sector, particularly for domestic and farm animals. The compounds are particularly effective against sucking, plant-damaging insects, especially aphids and leaf hoppers. Pesticidally active substituted 2-nitroguanidines of the type which can be produced according to the invention are described for example in EP patent applications 376.279, 375.907 and 383.091.

The starting compounds or starting products of formula (II), which may be considered for the process according to the invention, are partly known or may be produced by known processes. Where they are new, they similarly form an object of the invention.

TABLE C

Compounds of formula (IIa)

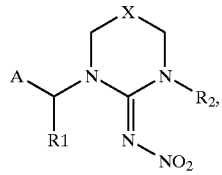

| No. | R$_1$ | R$_2$ | X |
|---|---|---|---|
| C.1 | H | H | O |
| C.2 | CH$_3$ | H | O |
| C.3 | H | H | S |
| C.4 | H | CH$_3$ | O |
| C.5 | CH$_3$ | CH$_3$ | O |
| C.6 | H | CH$_3$ | S |
| C.7 | H | C$_2$H$_5$ | O |
| C.8 | CH$_3$ | C$_2$H$_5$ | O |
| C.9 | C$_2$H$_5$ | C$_2$H$_5$ | O |
| C.10 | C$_2$H$_5$ | H | O |
| C.11 | H | C$_2$H$_5$ | S |
| C.12 | H | n-propyl | O |
| C.13 | H | n-propyl | S |
| C.14 | H | n-butyl | O |
| C.15 | H | isopropyl | O |
| C.16 | H | isobutyl | O |
| C.17 | H | sec-butyl | O |
| C.18 | H | tert-butyl | O |
| C.19 | H | cyclopropyl | O |
| C.20 | H | —CH$_2$—CH═CH$_2$ | O |
| C.21 | H | benzyl | O |
| C.22 | H | 4-Cl-benzyl | O |
| C.23 | H | 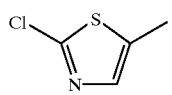 | O |

TABLE 1

Compounds of the general formula (IIa), wherein A is

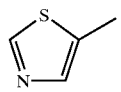

and R$_1$, R$_2$ and X each correspond to anyone of the lines of Table C.

TABLE 2

Compounds of the general formula (IIa), wherein A is

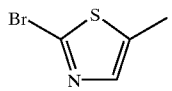

and R$_1$, R$_2$ and X each correspond to anyone of the lines of Table C.

TABLE 3

Compounds of the general formula (IIa), wherein A is

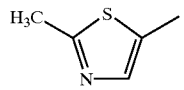

and R$_1$, R$_2$ and X each correspond to anyone of the lines of Table C.

TABLE 4

Compounds of the general formula (IIa), wherein A is

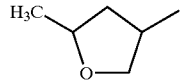

and R$_1$, R$_2$ and X each correspond to anyone of the lines of Table C.

TABLE 5

Compounds of the general formula (IIa), wherein A is

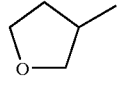

and R$_1$, R$_2$ and X each correspond to anyone of the lines of Table C.

TABLE 6

Compounds of the general formula (IIa), wherein A is

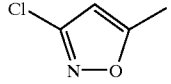

and R$_1$, R$_2$ and X each correspond to anyone of the lines of Table C.

TABLE 7

Compounds of the general formula (IIa), wherein A is and R$_1$, R$_2$ and X each correspond to anyone of the lines of Table C.

TABLE 8

Compounds of the general formula (IIa), wherein A is and R₁, R₂ and X each correspond to anyone of the lines of Table C.

TABLE 9

Compounds of the general formula (IIa), wherein A is and R₁, R₂ and X each correspond to anyone of the lines of Table C.

TABLE 10

Compounds of the general formula (IIa), wherein A is and R₁, R₂ and X each correspond to anyone of the lines of Table C.

TABLE 11

Compounds of the general formula (IIa), wherein A is and R₁, R₂ and X each correspond to anyone of the lines of Table C.

TABLE 12

Compounds of the general formula (IIa), wherein A is and R₁, R₂ and X each correspond to anyone of the lines of Table C.

PREPARATION EXAMPLES

Example 1

Preparation of 1-(2-chloropyrid-5-ylmethyl)-2-nitro-3-methyl-guanidine

A mixture of 4.0 g of 5-(2-chloropyrid-5-ylmethyl)-3-methyl-4-nitroimino-perhydro-1,3,5-oxadiazine and 20 ml of concentrated hydrochloric acid is stirred for 2 hours at 80° C. The reaction mixture is cooled to 5° C., adjusted to a pH of about 5 with concentrated caustic soda solution and filtered. The filtering residue is mixed with diethyl ether/ethyl acetate 1:1 and filtered again. The title compound is thus obtained.

Example 2

Preparation of 1-(2-chlorothiazol-5-ylmethyl)-2-nitro-3-methyl-guanidine

A mixture of 5.0 g of 5-(2-chlorothiazol-5-ylmethyl)-3-methyl4-nitroimino-perhydro-1,3,5-oxadiazine and 20 ml of concentrated hydrochloric acid is stirred for 2 hours at 80° C. The reaction mixture is cooled to 5° C., adjusted to a pH of about 5 with concentrated caustic soda solution and filtered. The filtering residue is mixed with diethyl ether/ethyl acetate 1:1 (v:v) and filtered again. The title compound is thus obtained.

The following compounds of formula (I) listed in Table 13 may also be obtained in analogous manner to the above procedures described in examples 1 and 2. c-propyl is cyclopropyl.

TABLE 13

Compounds of formula (I)

| Comp. No. | A | $R_1$ | $R_2$ |
|---|---|---|---|
| 13.1 | 2-chloro-pyrid-5-yl | H | H |
| 13.2 | 2-chloro-pyrid-5-yl | H | —CH₃ |
| 13.3 | 2-chloro-pyrid-5-yl | H | —C₂H₅ |
| 13.4 | 2-chloro-pyrid-5-yl | H | —C₃H₇(n) |
| 13.5 | 2-chloro-pyrid-5-yl | H | c-propyl |
| 13.6 | 2-chloro-pyrid-5-yl | H | —C₄H₉(n) |
| 13.7 | 2-chloro-pyrid-5-yl | H | —CH(CH₃)₂ |
| 13.8 | 2-chloro-pyrid-5-yl | —CH₃ | —CH₃ |
| 13.9 | 2-chloro-pyrid-5-yl | —C₂H₅ | —CH₃ |
| 13.10 | 2,3-dichloro-pyrid-5-yl | H | H |
| 13.11 | 2,3-dichloro-pyrid-5-yl | H | —CH₃ |
| 13.12 | 2,3-dichloro-pyrid-5-yl | H | —C₂H₅ |
| 13.13 | 2,3-dichloro-pyrid-5-yl | —CH₃ | —CH₃ |
| 13.14 | 2,3-dichloro-pyrid-5-yl | —C₂H₅ | —CH₃ |
| 13.15 | (pyridine N-oxide) | H | H |
| 13.16 | (pyridine N-oxide) | H | —CH₃ |
| 13.17 | (pyridine N-oxide) | H | —C₂H₅ |

TABLE 13-continued

Compounds of formula (I)

| Comp. No. | A | $R_1$ | $R_2$ |
|---|---|---|---|
| 13.18 | (3-methyl-pyridin-N-oxide) | H | c-propyl |
| 13.19 | (2-chloro-5-methyl-pyridin-N-oxide) | H | c-propyl |
| 13.20 | (2-chloro-5-methyl-pyridin-N-oxide) | —CH$_3$ | —CH$_3$ |
| 13.21 | 2-chloro-thiazol-5-yl | H | H |
| 13.22 | 2-chloro-thiazol-5-yl | H | —CH$_3$ |
| 13.23 | 2-chloro-thiazol-5-yl | —CH$_3$ | —CH$_3$ |
| 13.24 | 2-chloro-thiazol-5-yl | —C$_2$H$_5$ | —CH$_3$ |
| 13.25 | 2-chloro-thiazol-5-yl | H | —C$_2$H$_5$ |
| 13.26 | 2-chloro-thiazol-5-yl | H | c-propyl |
| 13.27 | 2-chloro-thiazol-5-yl | —CH$_3$ | c-propyl |
| 13.28 | tetrahydrofuran-3-yl | H | H |
| 13.29 | tetrahydrofuran-3-yl | H | —CH$_3$ |
| 13.30 | tetrahydrofuran-3-yl | H | —C$_2$H$_5$ |
| 13.31 | tetrahydrofuran-3-yl | H | c-propyl |
| 13.32 | tetrahydrofuran-3-yl | —CH$_3$ | —C$_2$H$_5$ |
| 13.33 | tetrahydrofuran-3-yl | —CH$_3$ | c-propyl |
| 13.34 | 5-methyl-tetrahydrofuran-3-yl | H | H |
| 13.35 | 5-methyl-tetrahydrofuran-3-yl | H | —CH$_3$ |
| 13.36 | 5-methyl-tetrahydrofuran-3-yl | H | —C$_2$H$_5$ |
| 13.37 | 5-methyl-tetrahydrofuran-3-yl | H | c-propyl |
| 13.38 | 5-methyl-tetrahydrofuran-3-yl | —CH$_3$ | —CH$_3$ |

What is claimed is:

1. Process for the production of a compound of formula (I)

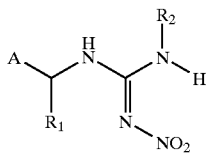

wherein $R_1$ is hydrogen or $C_1$–$C_4$-alkyl;

$R_2$ is hydrogen, $C_1$–$C_6$-alkyl, $C_2$–$C_6$-alkenyl, $C_2$–$C_6$-alkinyl, $C_3$–$C_6$-cycloalkyl or a radical —CH$_2$B;

A is selected from the group consisiting of 2-chloropyrid-5-yl, tetrahydrofuran-3-yl, 5-methyl-tetrahydrofuran-3-yl or 2-chlorothiazol-5-yl; and B is phenyl, 3-pyridyl or thiazolyl, which are optionally substituted by one to three substituents selected from the group consisting of $C_1$–$C_3$-alkyl, $C_1$–$C_3$-halogenalkyl, cyclopropyl, halogencyclopropyl, $C_2$–$C_3$-alkenyl, $C_2$–$C_3$-alkinyl, $C_1$–$C_3$-alkoxy, $C_2$–$C_3$-halogenalkenyl, $C_2$–$C_3$-halogenalkinyl, $C_1$–$C_3$-halogenalkoxy, $C_1$–$C_3$-alkylthio, $C_1$–$C_3$-halogenalkylthio, allyloxy, propargyloxy, allylthio, propargylthio, halogenallyloxy, halogenallylthio, halogen, cyano or nitro;

and optionally the possible E/Z isomers, E/Z isomeric mixtures or tautomers thereof, respectively in free form or in salt form;

characterised in that a compound of formula (II)

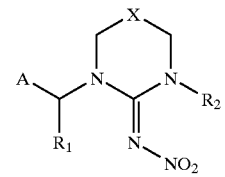

wherein $R_1$, $R_2$ and A have the same significances as in formula (I), and

X is O or S;

is hydrolysed with a strong acid at a pH below 2; at a temperature between 50 and 100° C.; and in a solvent selected from the group consisting of water, alcohols, ethers or mixtures thereof.

2. Process according to claim 1 for the production of a compound of formula (I) in free form.

3. Process according to claim 1 for the production of a compound of formula (I), wherein $R_1$ is hydrogen.

4. Process according to claim 1 for the production of a compound of formula (I), wherein $R_2$ is hydrogen, $C_1$–$C_3$-alkyl or cyclopropyl.

5. Process according to claim 1 for the production of a compound of formula (I) from a compound of formula (II), wherein X is O.

6. Process according to claim 1, characterised in that a mineral acid is employed.

7. Process according to claim 1, characterised in that the process is carried out in a solvent selected from the group consisting of water, alcohols, ethers or mixtures thereof.

* * * * *